(12) United States Patent
Franklin

(10) Patent No.: US 8,522,622 B2
(45) Date of Patent: Sep. 3, 2013

(54) COMBINED BENDING AND TORSION TEST SYSTEM AND METHOD

(75) Inventor: Walter Franklin, Canyon Country, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 218 days.

(21) Appl. No.: 13/099,230

(22) Filed: May 2, 2011

(65) Prior Publication Data

US 2012/0279312 A1   Nov. 8, 2012

(51) Int. Cl.
*G01N 3/08*   (2006.01)
(52) U.S. Cl.
USPC ............................................. 73/818; 73/760
(58) Field of Classification Search
USPC ............................................ 73/760, 818, 832
See application file for complete search history.

(56) References Cited

U.S. PATENT DOCUMENTS

| | | | |
|---|---|---|---|
| 3,283,567 A * | 11/1966 | Fietz | 73/84 |
| 3,693,424 A * | 9/1972 | Wagle | 73/114.78 |
| 4,308,666 A * | 1/1982 | Hahn et al. | 33/820 |
| 4,607,710 A * | 8/1986 | Radford | 175/249 |
| 4,884,638 A * | 12/1989 | Hoffman | 172/22 |
| 5,217,555 A * | 6/1993 | Franklin et al. | 156/156 |
| 6,578,433 B1 * | 6/2003 | Yakopson et al. | 73/832 |
| 7,383,889 B2 * | 6/2008 | Ring et al. | 166/382 |
| 2003/0173279 A1 * | 9/2003 | Aste | 210/198.2 |
| 2005/0056433 A1 * | 3/2005 | Ring et al. | 166/384 |

* cited by examiner

*Primary Examiner* — Max Noori
(74) *Attorney, Agent, or Firm* — McDermott Will & Emery LLP

(57) ABSTRACT

A fixture for testing a tubular member simultaneously in bending and torsion is disclosed. The fixture includes first and second attachment elements that are configured to couple to the tubular member, and a load shoe that is configured to fit within the tubular member. The load shoe includes a body having a contact surface configured to contact a portion of an internal surface of the tubular member and at least one load reaction strut coupled to the body. The load reaction strut is configured to pass through a hole in the tubular member and accept a first force applied in a first direction that is perpendicular to an axis of symmetry of the tubular member.

15 Claims, 4 Drawing Sheets

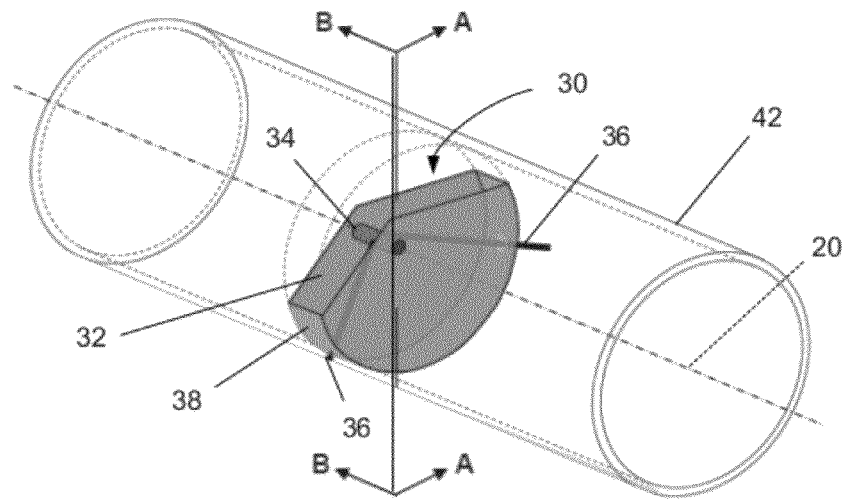
FIG. 4A
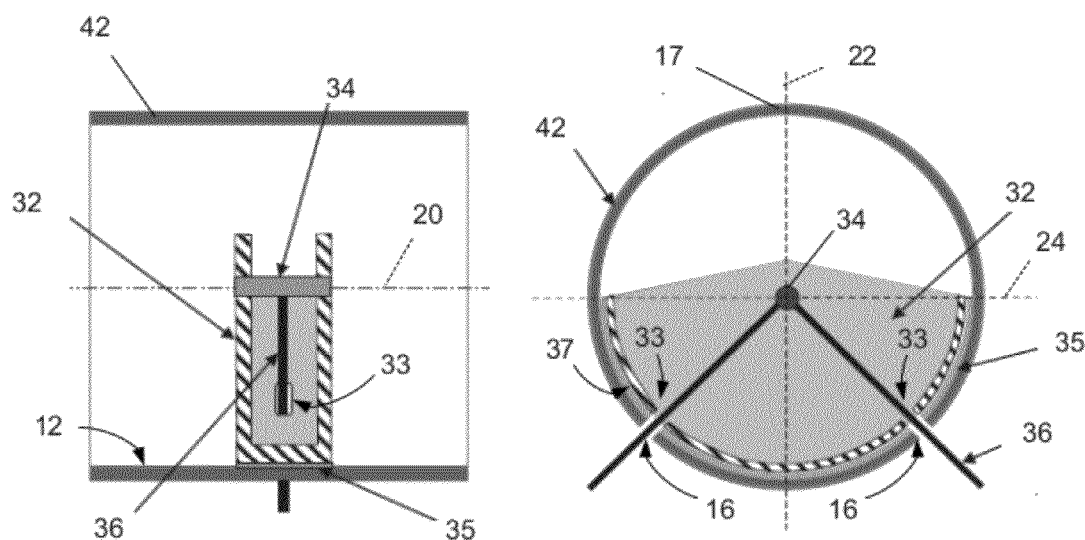
(VIEW A-A OF FIG. 3A)
FIG. 4B
(VIEW B-B OF FIG. 3A)
FIG. 4C

COMBINED BENDING AND TORSION TEST SYSTEM AND METHOD

CROSS-REFERENCE TO RELATED APPLICATIONS

Not applicable.

STATEMENT REGARDING FEDERALLY SPONSORED RESEARCH OR DEVELOPMENT

Not applicable

BACKGROUND

1. Field

The present disclosure generally relates to testing methods and, in particular, testing a tubular member simultaneously in bending and torsion.

2. Description of the Related Art

Thin-walled tubular structural members are sometimes used in applications where the member is subjected to combined bending and torsional loads. For example, tubular members may be used as part of the structure of a wing or tail of an aircraft. It is often desirable to test the performance of these structural members to determine their true capabilities and thereby increase the confidence in the design.

Current methods of performing bending and torsional tests of thin-walled tubular members present a number of difficulties. Bending tests are commonly performed by the application of a lateral load to the midpoint of the tubular member. For very thin-walled tubes, performing a bending test alone can be problematic due to the tendency of any test fixture restraint to crush or damage the tube wall. In addition, one failure mode of a bending test is a buckling failure in the exact region where the lateral load is applied, raising the potential that the test fixture will interfere with the failure mode. In these cases, an edgewise compression test is sometimes used as a compromise approach, but this type of test may not capture the true bending and buckling stability capability of the tubular member.

If a torsional load is applied at the same time as the lateral load, the portion of the fixture that is applying the lateral load may induce an inadvertent torsional restraint in the test. The local stresses created by the application of the side load and the inadvertent torsional restraint at the midpoint may result in a failure at the midpoint due to stress conditions that are not representative of the true condition in service.

To avoid the problems and uncertainties related to performing a combined bending and torsion test of a thin-walled tubular member, bending and torsion tests are often performed separately and combined by analytical means, which introduces uncertainties that may preclude achieving minimum weight structure.

SUMMARY

There is a need to simultaneously perform accurate and realistic bending and torsion tests of thin-walled tubular members. The disclosed system and method provide a means of accomplishing this testing without the drawbacks of current methods and equipment.

The disclosed system includes a load shoe that fits within the tubular member under test. The load shoe conforms to the lower portion of the interior surface of the tubular member to evenly apply the lateral load. Application of the load in this area avoids interaction with the buckling behavior of the upper portion of the tubular member that is in compression. The load shoe incorporates struts that protrude through small holes in the lower wall of the tubular member in regions that will not influence the test results. Loads applied in pure tension to these struts results in a net lateral load on the tubular member. The struts are attached to the load shoe through a rotating shaft such that torsional loads are transmitted down the length of the tubular member without inducing a reaction load on the struts. Use of this load shoe enables a tubular member to be realistically tested simultaneously in bending and torsion, enabling the designers to achieve a minimum weight structure while maintaining the necessary safety margins.

In certain embodiments, a fixture for testing a tubular member is disclosed. The fixture includes first and second attachment elements that are configured to couple to the tubular member, and a load shoe configured to fit within the tubular member. The load shoe includes a body having a contact surface configured to contact a portion of an internal surface of the tubular member and at least one load reaction strut coupled to the body. The load reaction strut is configured to pass through a hole in the tubular member and accept a first force applied in a first direction that is perpendicular to an axis of symmetry of the tubular member.

In certain embodiments, a load shoe for applying a lateral load to a tubular member is disclosed. The load shoe includes a body having a contact surface configured to contact a portion of an internal surface of the tubular member and at least one load reaction strut coupled to the body. The load reaction strut configured to pass through a hole in the tubular member and accept a first force applied in a first direction that is perpendicular to an axis of symmetry of the tubular member.

In certain embodiments, a method of apply a lateral load to a tubular member is disclosed. The method includes the steps of placing a load shoe comprising a contact surface configured to contact a portion of an internal surface of the tubular member and at least one load reaction strut configured to pass through a hole in the tubular member within the tubular member such that the at least one load reaction strut extends through a hole in the tubular member, and applying the lateral load to the at least one load reaction strut.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 4A is a perspective view of a load shoe and tubular test element according to certain aspects of this disclosure.

FIGS. 4B and 4C are cross-sections of the load shoe and tubular test element of FIG. 4A according to certain aspects of this disclosure.

DETAILED DESCRIPTION

Testing of extremely light-weight, thin-walled, tubular structural members subjected to combined bending and torsional loads presents several challenges regarding the design of fixtures required to react the applied loads and restrain the test article. These challenges include: (1) how to provide restraint to the tubular test section to react the applied vertical loads and not crush the test section, (2) how to provide this vertical restraint and not interfere with the buckling behavior of the upper compression surface of the tube, (3) how to provide vertical restraint and still allow the torsional moment to be transmitted freely through the length of the test section. The disclosed system and method provide at least an improvement in meeting these challenges.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The method and system disclosed herein are presented in terms of a thin-walled tubular structural member. It will be obvious to those of ordinary skill in the art that this same configuration and method can be utilized in a variety of applications wherein there is a desire to apply a lateral load to a hollow element. Nothing in this disclosure should be interpreted, unless specifically stated as such, to limit the application of any method or system disclosed herein to a testing of thin-walled tubular members.

Figure 1:
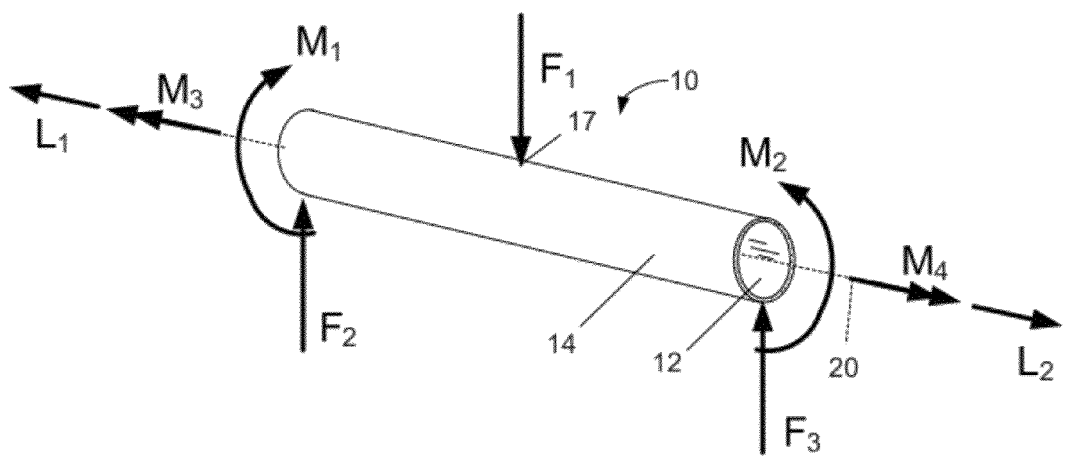
FIG. 1 is a free-body diagram illustrating exemplary load tests to be performed on a thin-walled tubular member.

FIG. 1 is a free-body diagram illustrating exemplary load tests to be performed on a thin-walled tubular member 10. In this example, a bending load is created by the application of force $F_1$ at the point 17 at the midpoint of the tubular member 10 with corresponding forces $F_2$ and $F_3$ applied in the opposite direction at the ends of the tubular member 10. A bending load is also applied by the application of moments $M_1$ and $M_2$ in the plane 22 of FIG. 2. A torsional load is applied by the application of moments $M_3$ and $M_4$ in opposite directions at the ends of the tubular member 10. In this example, a tension load is also applied by loads $L_1$ and $L_2$ in opposite directions at the ends of the tubular member 10. If the loads $F_1$, $F_2$ are negative (i.e., the load vectors pointed in the opposite directions), a compressive load would created in the tubular member 10.

Figure 2:
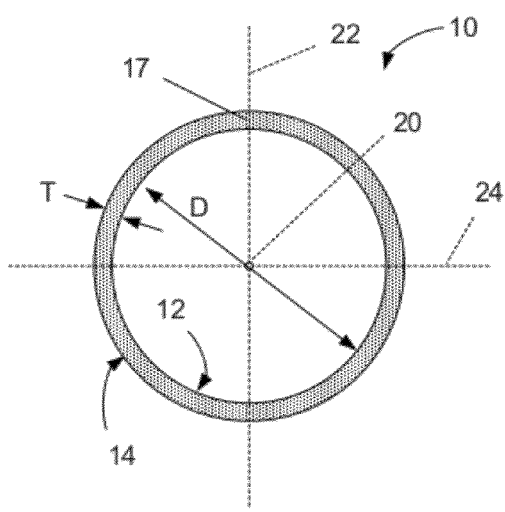
FIG. 2 is a cross-section of the tubular member of FIG. 1.

FIG. 2 is a cross-section of the tubular member 10 of FIG. 1. The tubular member 10 has an interior surface 12 and an exterior surface 14. There is a centerline 20 along the length of the tubular member 10, coming out of the page as seen in FIG. 2. A first plane 22 is defined as including the centerline 20, with a second plane 24 also including the centerline 20 and perpendicular to the first plane 22. The tubular member 10 also is characterized by an inner diameter D and a wall thickness T. In the embodiment shown in FIG. 1, point 17 is coincident with plane 22.

Figure 3A:
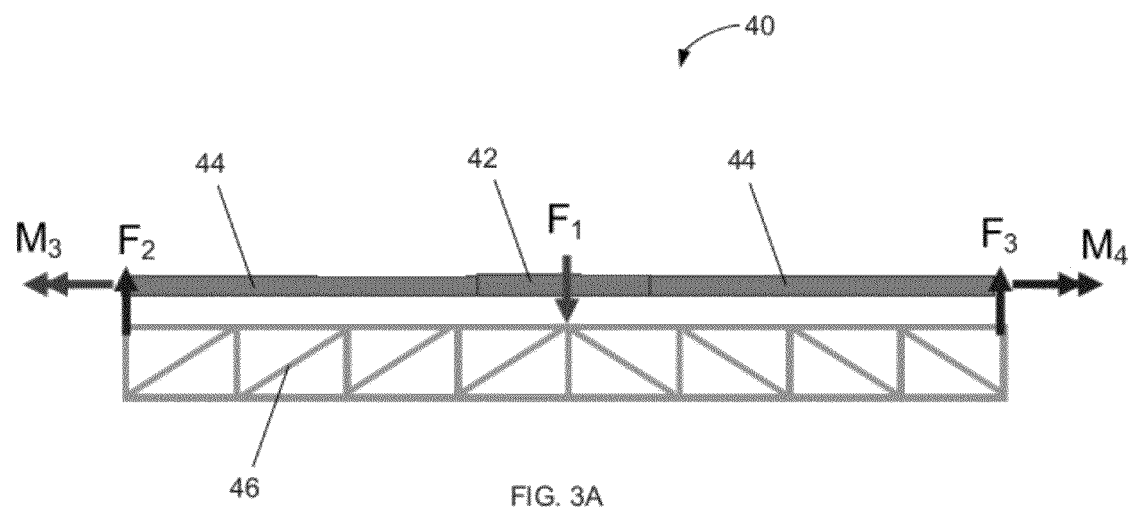
FIGS. 3A and 3B illustrate an exemplary test fixture according to certain aspects of this disclosure.
Figure 3B:
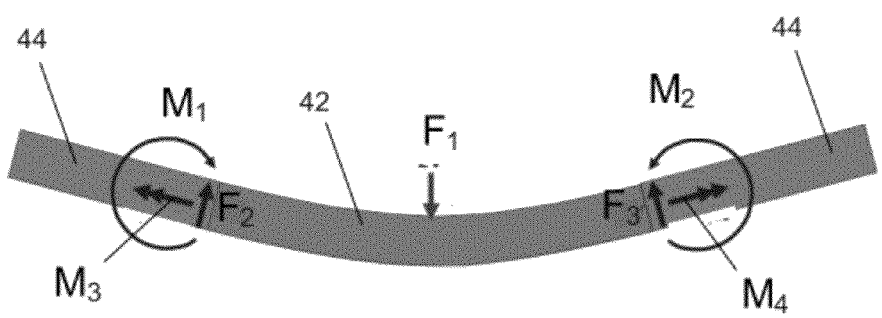

FIGS. 3A and 3B illustrate an exemplary test fixture 40 according to certain aspects of this disclosure. FIG. 3A illustrates a tubular test element 42 of the tubular member 10 connected to load application tubes 44 at each end. The load application tubes are rigid in comparison to the tubular test element 42 so that deformation occurs primarily in the tubular test element 42. In certain embodiments, the load application tubes 44 are solid rods. In certain applications, the load application tubes 44 are larger in diameter than the tubular test element 42. Application of shear loads $F_2$ and $F_3$ create moments at the ends of tubular test element 42. A load F1 is applied at the middle of test element 42. Torques M3 and M4 are applied to the ends of the load application tubes 44 to create a torque load in the tubular test element 42. The test fixture truss 46 provides a rigid reference for the actuators that apply the loads and torques to the tubular test element 42.

FIG. 3B is an enlarged view of the tubular test element 42 of FIG. 3A. The forces and moments present at the interface between the load application tubes 44 and the tubular test element 42 (i.e., the ends of the tubular test element 42) are shown in FIG. 3B. The forces F2 and F3 applied to the outer ends of the load application tubes 44 have created moments M1 and M2 at the ends of the tubular test element 42, as previously discussed with respect to FIG. 1, as well as the forces F2 and F3 being transferred through the load application tubes 44 to the ends of the tubular test element 42. Moments M3 and M4 have also been transferred to the ends of tubular test element 42.

FIG. 4A is a perspective view of a load shoe 30 and tubular test element 42 according to certain aspects of this disclosure. In this embodiment, the load shoe 30 has a hollow body 32 with a contact face 37 (not visible in FIG. 4A). A compliant layer 38, such as a rubber pad, covers the surface 37 of the body 32. A pin 34 is rotatably coupled to the body 32 such that the pin 34 is located at the centerline 20 of the tubular test element 42 when the load shoe 30 is installed within the tubular test element 42. In this embodiment, two load reaction struts 36 are fixedly coupled to the pin 34 and extend out through holes 33 in the body 32 of the load shoe 30 as well as through holes 16 in the tubular test element 42. The holes are sized such that the expected deformation of the tubular test element 42 will not cause the struts 36, which will remain fixed in position and orientation relative to the test fixture truss 46, to contact either the body 32 or the tubular test element 42. The interaction between the load shoe 30 and the tubular test element 42 are discussed in greater detail with respect to FIGS. 4B-4C and 5A-5B.

FIGS. 4B and 4C are cross-sections of the load shoe 30 and tubular test element 42 of FIG. 4A according to certain aspects of this disclosure. FIG. 4B is a cross-section taken along section line A-A through the center of load shoe 30 in FIG. 4A. In FIG. 4B, it can be seen that the pin 34 is on the centerline 20. This ensures that rotation of the tubular test element 42 that may be induced by the applied torques of moment M3 and M4 do not displace the point of application of the loads applied through the struts 36. The external surface 35 of the compliant layer 38 can be seen to be in contact with the interior surface 12 of the tubular test element 42.

FIG. 4C is a cross-section taken on section line B-B through the center of load shoe 30 in FIG. 4A. FIG. 4C illustrates how the profile of the contact face 37 of the body 32 and therefore the profile of the external surface 35 of the compliant layer 38 are matched to the inside diameter D of the tubular test element 42. As such, a different load shoe 30 is required for each different inner diameter D of tubular test elements 42. It can be seen how the struts 36 pas through the holes 33 and 16 in the body 32 and tubular test element 42, respectively. The holes 16 in the tubular test element 42 shown in FIG. 4C are not in areas of the wall of tubular test element 42 that are highly stressed or expected to be the points of failure, as this test load combination is usually expected to fail in buckling at point 17. As the lateral load Fl is now applied through the struts 36, as is discussed in greater detail with respect to FIG. 5B, rather than at the surface at point 17, the load application method does not distort the buckling behavior of tubular test element 42 at point 17. As no test load is applied directly at point 17, the stresses at point 17 are solely the result of the applied moments M1 and M2, forces F1, F2, and F3, and the torque created by moment M3 and M4.

If one of the load application tubes 44 is restrained from rotating at one outer end, with the other load application tube 44 free to rotate, application of moments M3 and M4 may cause the tubular test element 42 to rotate with respect to a test fixture such as the truss 46. The orientation of the load show 30 will remain fixed with respect to the test fixture. The holes 16 in the wall of tubular test element 42 need to be large enough to ensure that this rotation of the tubular test element 42 does not cause the edges of the holes 16 to contact the struts 36. As the rotation of tubular test element 42 is expected to be small, especially if the tubular test element is a composite structure, the size of the holes 16 will remain small enough to not detrimentally affect the stress patterns in the tubular test element 42.

The profile seen in FIG. 4C of the body 32 can be seen to contact the interior surface 12 of the tubular test element 42 over the lower portion, i.e. the 180 degree region below plane 24. This lower portion of tubular test element 42 is expected to be in tension in this test arrangement and is not expected to be a region of failure. Therefore, application of a lateral load through the compliant layer 28 over the lower portion of tubular test element 42 is expected to have little, if any, effect on the performance or failure mode of the tubular test element 42. In certain embodiments, the body 32 and compliant layer 38 contact less than a 180 degree portion of the interior surface 12.

Figure 5A:
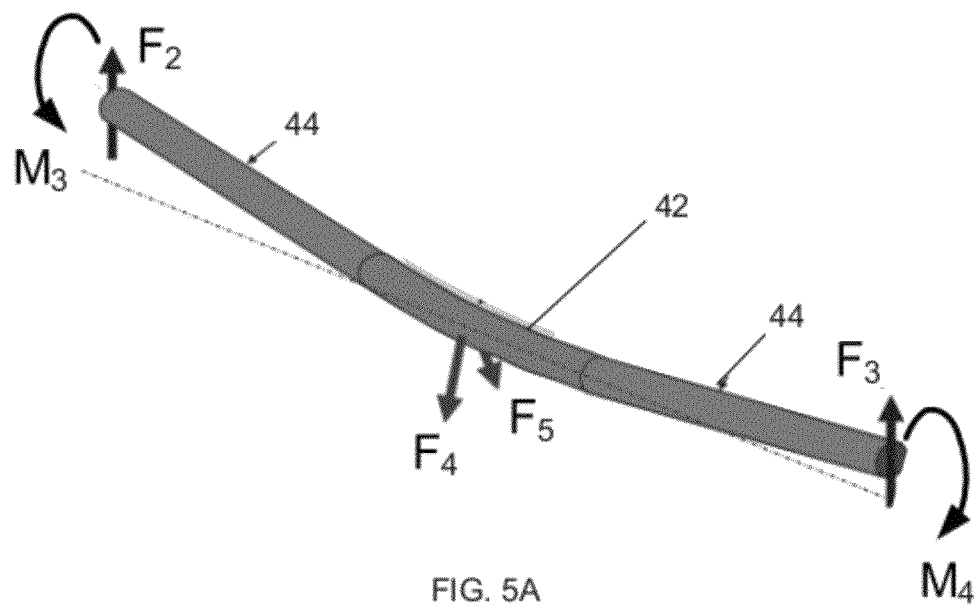
FIG. 5A is a perspective view of a tubular test element under test using the load shoe of FIG. 4A according to certain aspects of this disclosure.
Figure 5B:
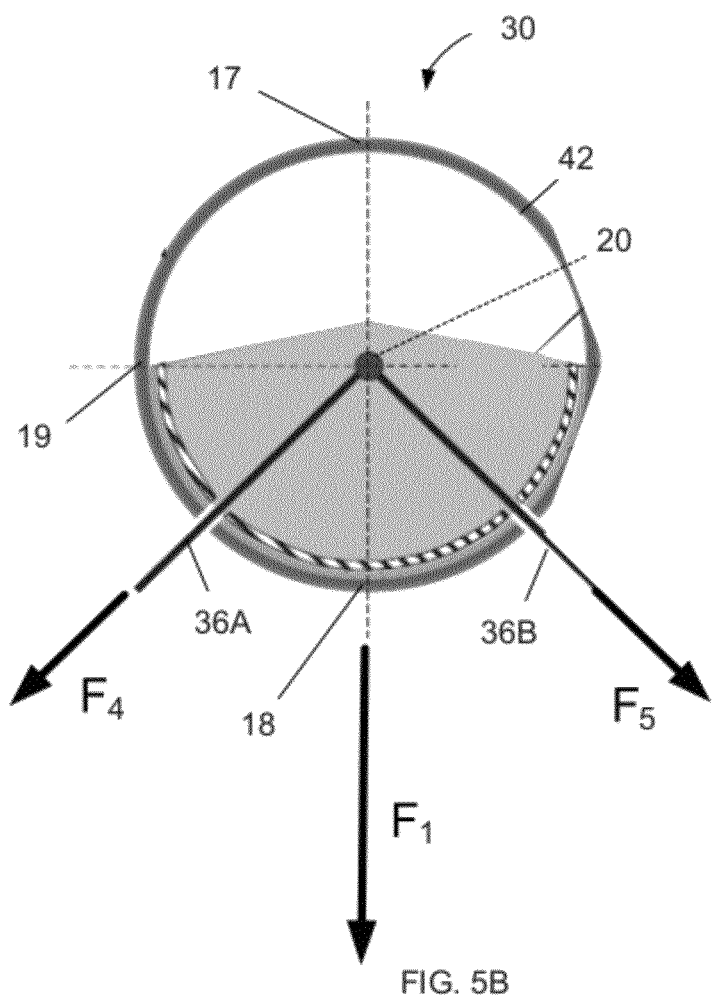
FIG. 5B is a cross-section of the load shoe and tubular test element of FIG. 5A according to certain aspects of this disclosure.

FIG. 5A is a perspective view of a tubular test element 42 under test using the load shoe 30 of FIG. 4A according to certain aspects of this disclosure. Load extension tubes 44 are connected at their inner ends to the ends of tubular test element 42. In this embodiment, a torque in tubular test element 42 is applied by the combination of moments M3 and M4 applied to the outer ends of the load extension tubes 44. A downward lateral force at the middle of tubular test element 42 is created through the combination of forces F4 and F5 that are respectively applied in line with the two struts 36A and 36B, producing a net force F1 as shown in FIG. 5B. Lateral loads F2 and F3, are applied at the outer ends of the load extension tubes, wherein the vector sum of loads F2 and F3 is equal in magnitude and opposite in direction to the net load F1.

FIG. 5B is a cross-section of the load shoe 30 and tubular test element 42 of FIG. 5A according to certain aspects of this disclosure. It can be seen how the loads F4 and F5 are applied in line with the struts 36A and 36B, resulting in a net force F1 applied through the centerline 20. It can be seen that the compliant layer 38 contacts the interior surface 12 over the lower 180 degree portion of the tubular test element 42 at point 17. As the net load F1 is applied downward, in this embodiment, the contact force between the compliant layer 38 and the interior surface 12 at point 19, i.e. at the neutral axis of tubular test element 42 when bent in the manner illustrated in FIG. 5A, is approximately zero. The maximum tensile stress created in the wall of tubular test element 42 may occur, in some test configurations, at point 18 where the load shoe does not apply a point load and has little or no effect on the stress or failure at this point.

The concepts disclosed herein provide a method of simultaneously applying a torque and a bending moment to a tubular element that reduces the distortion induced by test fixture on the stresses in the expected failure areas. The load shoe disclosed herein provides a method of applying a lateral load to the portion of the tubular test element that is in tension. The load shoe also applies the lateral load over an extended area rather than at a point, avoiding local damage to the tubular element under test. The use of a load shoe of the type disclosed herein allows realistic testing of combined bending and torsion loads that may result in a lower component weight while maintaining adequate performance and safety margins.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A fixture for testing a tubular member, the fixture comprising:
   first and second attachment elements configured to couple to the tubular member;
   a load shoe configured to fit within the tubular member, the load shoe comprising:
      a body having a contact surface configured to contact a portion of an internal surface of the tubular member; and
      at least one load reaction strut coupled to the body, the load reaction strut configured to pass through a hole in the tubular member and accept a first force applied in a first direction that is perpendicular to an axis of symmetry of the tubular member.

2. The fixture of claim 1, wherein the first and second attachment elements are configured to cooperatively apply to the tubular member at least one of a reaction force to the first force, a tension load, a compression load, a torsion load, and a bending load.

3. The fixture of claim 1, wherein the at least one load reaction strut is rotatable coupled to the body at a point coincident with the axis of symmetry of the tubular member when the load shoe is positioned within the tubular member.

4. The fixture of claim 3, wherein:
   the load shoe further comprises a pin;
   the pin is rotatable coupled to the body at the point coincident with the axis of symmetry of the tubular member; and
   the at least one load reaction strut is fixedly coupled to the pin.

5. The fixture of claim 4, wherein the load shoe comprises two load reaction struts that are fixedly coupled to the pin, the load reaction struts configured to respectively pass through two holes in the tubular member that are not on a vertical centerline of the tubular member.

6. The fixture of claim 5, wherein the two load reaction struts are configured to accept application of two second forces, the vector sum of the second forces creating the first force.

7. The fixture of claim 6, wherein the two second forces put the two load reaction struts solely in tension.

8. The fixture of claim 1, wherein:
   the load shoe further comprises a compliant pad that is coupled to the contact surface; and
   the contact surface and compliant pad are configured such that an external surface of the compliant pad contacts the portion of the internal surface of the tubular member.

9. A load shoe for applying a lateral load to a tubular member, the load shoe comprising:
   a body having a contact surface configured to contact a portion of an internal surface of the tubular member; and
   at least one load reaction strut coupled to the body, the load reaction strut configured to pass through a hole in the tubular member and accept a first force applied in a first direction that is perpendicular to an axis of symmetry of the tubular member.

10. The load shoe of claim 9, further comprising a pin that is rotatable coupled to the body at the point coincident with the axis of symmetry of the tubular member and fixedly coupled to the at least one load reaction strut.

11. The load shoe of claim 10, wherein the load shoe comprises two load reaction struts that are fixedly coupled to the pin, the load reaction struts configured to respectively pass through two holes in the tubular member that are not on a vertical centerline of the tubular member and accept application of two second forces, the vector sum of the second forces creating the first force.

12. The load shoe of claim 9, further comprising a compliant pad that is coupled to the contact surface, wherein the contact surface and compliant pad are configured such that an external surface of the compliant pad contacts the portion of the internal surface of the tubular member.

13. A method of apply a lateral load to a tubular member, the method comprising the steps of:
   placing a load shoe comprising a contact surface configured to contact a portion of an internal surface of the tubular member and at least one load reaction strut configured to pass through a hole in the tubular member within the tubular member such that the at least one load reaction strut extends through a hole in the tubular member; and
   applying the lateral load to the at least one load reaction strut.

14. The method of claim 13, wherein:
   the load shoe comprises two load reaction struts configured to respectively pass through two holes in the tubular member that are not on a vertical centerline of the tubular member; and
   the step of applying the lateral load comprises applying two forces respectively to the two load reaction struts, the vector sum of the applied forces creating the lateral load.

15. The method of claim 13, further comprising the step of:
   applying at least one of a reaction force to the first force, a tension load, a compression load, a torsion load, and a bending load through first and second attachment elements that are coupled to the tubular member.

* * * * *